United States Patent
Koltz, Jr. et al.

(10) Patent No.: US 12,053,572 B2
(45) Date of Patent: Aug. 6, 2024

(54) SURGICAL GAS DELIVERY SYSTEM AND METHOD FOR GAS SEALED INSUFFLATION AND RECIRCULATION USING PROPORTIONAL VALVES

(71) Applicant: Conmed Corporation, Utica, NY (US)

(72) Inventors: Michael Koltz, Jr., Aurora, CO (US); Jonathan Teymouri, Aurora, CO (US)

(73) Assignee: Conmed Corporation, Largo, FL (US)

( * ) Notice: Subject to any disclaimer, the term of this patent is extended or adjusted under 35 U.S.C. 154(b) by 303 days.

(21) Appl. No.: 17/155,572

(22) Filed: Jan. 22, 2021

(65) Prior Publication Data
US 2022/0233791 A1    Jul. 28, 2022

(51) Int. Cl.
*A61M 13/00* (2006.01)
*A61B 17/34* (2006.01)

(52) U.S. Cl.
CPC ....... *A61M 13/006* (2014.02); *A61B 17/3423* (2013.01); *A61B 17/3462* (2013.01); *A61B 2217/005* (2013.01); *A61M 2205/3331* (2013.01); *A61M 2205/36* (2013.01)

(58) Field of Classification Search
CPC .. A61M 13/00; A61M 13/003; A61M 13/006; A61M 2205/3331; A61M 2205/36; A61M 5/16881; A61M 39/22; A61M 5/16877; A61M 39/227; A61M 39/228; A61M 39/225; A61M 2039/226; A61M 2039/242; A61M 16/20; A61M 16/201; A61M 16/202; A61M 16/203; A61M 16/204; A61M 16/205; A61M 16/208; A61M 16/209; A61M 2205/128; A61M 2205/12; A61M 2205/3337; A61M 2205/3341; A61B 17/3423; A61B 17/3462; A61B 2217/005
See application file for complete search history.

(56) References Cited

U.S. PATENT DOCUMENTS

| | | | |
|---|---|---|---|
| 5,354,268 A * | 10/1994 | Peterson | A61M 1/74 604/35 |
| 7,854,724 B2 | 12/2010 | Stearns et al. | |
| 8,795,223 B2 | 8/2014 | Stearns et al. | |
| 9,199,047 B2 * | 12/2015 | Stearns | A61M 13/003 |
| 9,375,539 B2 | 6/2016 | Stearns et al. | |

(Continued)

*Primary Examiner* — Kami A Bosworth
*Assistant Examiner* — Avery Smale
(74) *Attorney, Agent, or Firm* — Locke Lord LLP; Scott D. Wofsy

(57) ABSTRACT

A surgical gas delivery system is disclosed for gas sealed insufflation and recirculation, which includes a gaseous sealing manifold for communicating with a gas sealed access port, an insufflation manifold for communicating with the gas sealed access port and with a valve sealed access port, a compressor for recirculating gas through the gas sealed access port by way of the gaseous sealing manifold, a first outlet line valve associated with the insufflation manifold for controlling a flow of insufflation gas to the gas sealed access port, a second outlet line valve associated with the insufflation manifold for controlling a flow of insufflation gas to the valve sealed access port, and a proportional valve associated the insufflation manifold and located upstream from the first and second outlet line valves for dynamically controlling the flow of insufflation gas to the first and second outlet line valves.

25 Claims, 1 Drawing Sheet

(56) References Cited

U.S. PATENT DOCUMENTS

| | | | |
|---|---|---|---|
| 10,384,021 B2 | 8/2019 | Koeth et al. | |
| 10,702,306 B2 | 7/2020 | Silver et al. | |
| 2007/0249990 A1* | 10/2007 | Cosmescu | A61M 13/003 604/23 |
| 2011/0282273 A1* | 11/2011 | Evans | A61M 13/003 604/24 |
| 2014/0236074 A1* | 8/2014 | Faif | A61M 16/026 604/26 |
| 2018/0214631 A1* | 8/2018 | Amirouche | A61M 5/142 |
| 2021/0178110 A1* | 6/2021 | Barnes | A61M 16/206 |

* cited by examiner

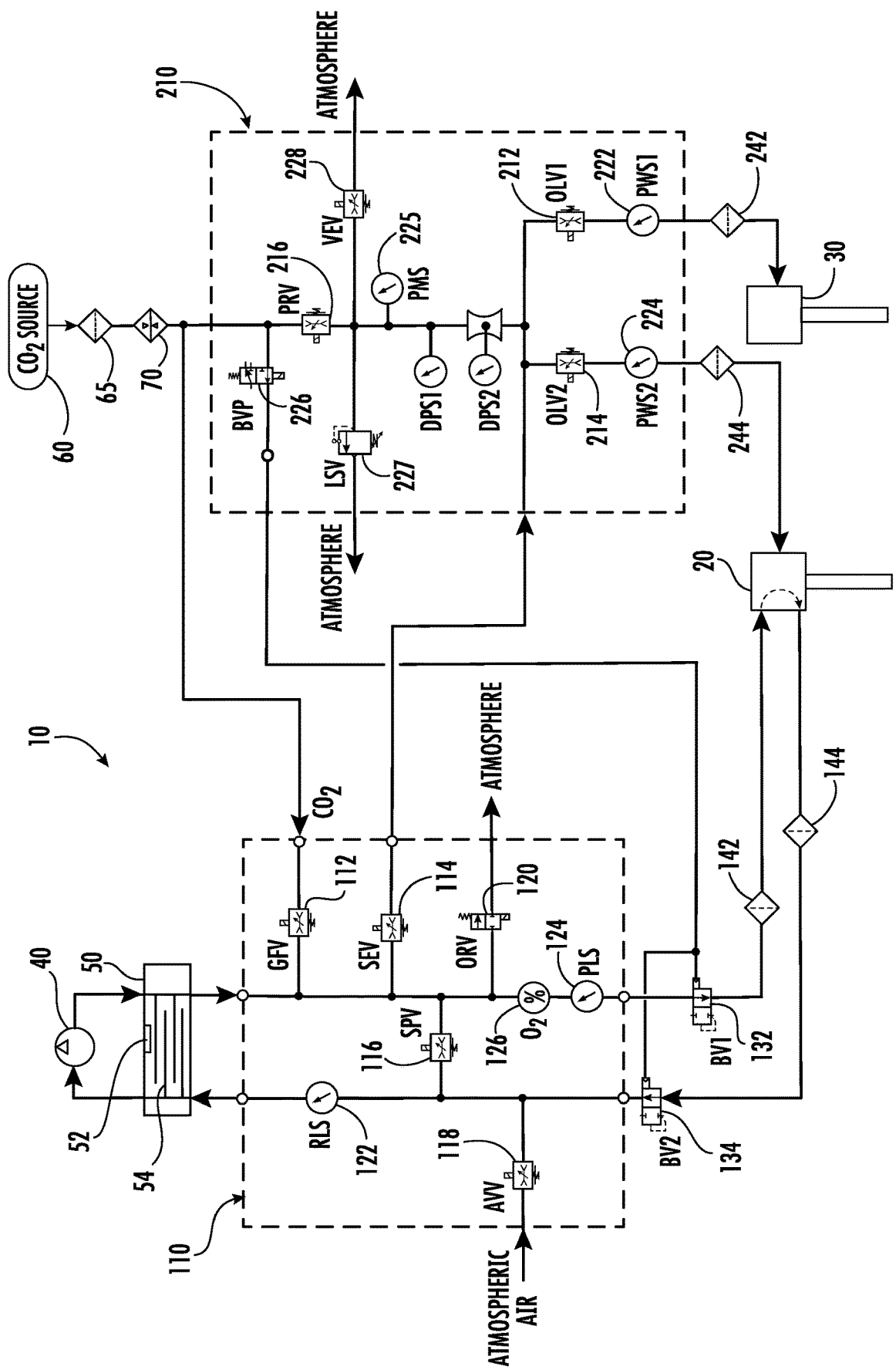

SURGICAL GAS DELIVERY SYSTEM AND METHOD FOR GAS SEALED INSUFFLATION AND RECIRCULATION USING PROPORTIONAL VALVES

BACKGROUND OF THE INVENTION

1. Field of the Invention

The subject invention is directed to minimally invasive surgery, and more particularly, to a surgical gas delivery system and method for gas sealed insufflation and recirculation that utilizes one or more proportional valves for dynamically controlling gas flow during an endoscopic or laparoscopic surgical procedure.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal cavity with a pressurized fluid, such as carbon dioxide, to create an operating space, which is referred to as a pneumoperitoneum. The insufflation can be carried out by a surgical access device, such as a trocar, equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, often using a separate inserter or obturator placed therein. Following insertion, the obturator is removed, and the trocar allows access for instruments to be inserted into the abdominal cavity. Typical trocars provide a pathway to insufflate the abdominal cavity, so that the surgeon has an open interior space in which to work.

The trocar must also provide a way to maintain the pressure within the cavity by sealing between the trocar and the surgical instrument being used, while still allowing at least a minimum amount of freedom of movement for the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas from the abdominal cavity. These sealing mechanisms often comprise a duckbill-type valve made of a relatively pliable material, to seal around an outer surface of surgical instruments passing through the trocar.

SurgiQuest, Inc., a wholly owned subsidiary of ConMed Corporation has developed unique gas sealed surgical access devices that permit ready access to an insufflated surgical cavity without the need for conventional mechanical valve seals, as described, for example, in U.S. Pat. Nos. 7,854,724 and 8,795,223. These access devices are constructed from several nested components including an inner tubular body portion and a coaxial outer tubular body portion. The inner tubular body portion defines a gas sealed central lumen for introducing conventional laparoscopic or endoscopic surgical instruments to the surgical cavity of a patient and the outer tubular body portion defines an annular lumen surrounding the inner tubular body portion for delivering insufflation gas to the surgical cavity of the patient and for facilitating periodic sensing of abdominal pressure.

SurgiQuest has also developed multimodal surgical gas delivery systems for use with the unique gas sealed access devices described above. These gas delivery systems, which are disclosed for example in U.S. Pat. Nos. 9,199,047 and 9,375,539 have a first mode of operation for providing gas sealed access to a body cavity, a second mode of operation for performing smoke evacuation from the body cavity, and a third mode of operation for providing insufflation gas to the body cavity.

In the prior art SurgiQuest gas delivery system, the delivery or outflow of insufflation gas to the body cavity is controlled by solenoid valves, which have certain limitations with respect to the ability to control gas flow rates dynamically. For example, a solenoid valve with a 6 mm orifice has two flow states: zero and the 6 mm orifice flow as a function of the differential pressure. However, a 6 mm orifice proportional valve has an infinite number of intermediate flow settings, or equivalent orifice diameters.

Since flow is a function of the square of the orifice diameter, the additional intermediate valve positions of a proportional valve provide fine control beyond a simple linear relationship, as well as the ability to achieve stable flow rates at lower pressure, reduce pressure oscillation and eliminate pneumatic hammer. Furthermore, the first 10% of valve opening, or an effective orifice diameter of 0.6 mm, modulates one percent ($10\%^2$) of full-open flow; which could be favorable in pediatric applications.

SUMMARY OF THE DISCLOSURE

A new and useful surgical gas delivery system is disclosed for gas sealed insufflation and recirculation during an endoscopic or laparoscopic surgical procedure. The gas delivery system includes a gaseous sealing manifold for communicating with a gas sealed access port, an insufflation manifold for communicating with the gas sealed access port and with a valve sealed access port and a compressor for recirculating gas through the gas sealed access port by way of the gaseous sealing manifold.

The system further includes a first proportional outlet line valve operatively associated with the insufflation manifold for dynamically controlling a flow of insufflation gas to the gas sealed access port, and a second proportional outlet line valve operatively associated with the insufflation manifold for dynamically controlling a flow of insufflation gas to the valve sealed access port. In addition, the insufflation manifold includes a first pressure sensor downstream from the first outlet line valve and a second pressure sensor downstream from the second outlet line valve, and wherein two other pressure sensors are situated within a venture tube to maintain a pressure differential that is used to infer a gas flow rate proximal to the access ports.

The system also includes a source of surgical gas that communicates with the gaseous sealing manifold and the insufflation manifold. Gas from the surgical gas source flows through a high pressure regulator and a gas heater before the gas is delivered to the gaseous sealing manifold and the insufflation manifold.

The gaseous sealing manifold includes a gas fill valve that is operatively associated with an outlet side of the compressor for controlling gas delivered into the gaseous sealing manifold from the source of surgical gas, and preferably the gas fill valve is a proportional valve. The gaseous sealing manifold also includes a smoke evacuation valve that is operatively associated with an outlet side of the compressor for controlling gas flow between the gaseous sealing manifold and the insufflation manifold under certain operating conditions, and the smoke evacuation valve is preferably a proportional valve.

The gaseous sealing manifold also includes a bypass valve that is located between an outlet side of the compressor and an inlet side of the compressor for controlling gas flow within the gaseous sealing manifold under certain operating conditions, and the bypass valve is preferably a proportional valve. And, the gaseous sealing manifold includes an air ventilation valve that is operatively associated with an inlet side of the compressor for controlling entrainment of atmospheric air into the system under certain operating conditions, and the air ventilation valve is preferably a proportional valve.

The gaseous sealing manifold further includes an overpressure relief valve that is operatively associated with an outlet side of the compressor for controlling a release of gas from the system to atmosphere under certain operating conditions, and the overpressure relief valve is preferably a solenoid valve. In addition, the gaseous sealing manifold includes a first pressure sensor that is operatively associated with an inlet side of the compressor and a second pressure sensor that is operatively associated with an outlet side of the compressor.

The gaseous sealing manifold also includes a gas quality sensor that is operatively associated with an outlet side of the compressor. Also, a first blocking valve is operatively associated with an inlet to the gaseous sealing manifold and a second blocking valve is operatively associated with an outlet to the gaseous sealing manifold, and preferably the first and second blocking valves are pneumatically actuated. In addition, the first and second blocking valves communicate with a blocking valve pilot that is included within with the insufflation manifold, and the blocking valve pilot is a solenoid valve.

The insufflation manifold also includes a low pressure safety valve located upstream from the outlet line valves for controlling a release of gas from the system to atmosphere under certain operating conditions. The insufflation manifold further includes a ventilation exhaust valve that is located upstream from the outlet line valves for controlling a release of gas from the system to atmosphere under certain operating conditions, and the ventilation exhaust valve is preferably a proportional valve. The insufflation manifold includes a proportional valve that is located upstream from the low pressure safety valve and the ventilation exhaust valve for maintaining a constant intermediate pressure within the system.

The subject invention is also directed to a surgical gas delivery system for gas sealed insufflation and recirculation that includes a gaseous sealing manifold for communicating with a gas sealed access port, a compressor for recirculating gas through the gas sealed access port by way of the gaseous sealing manifold, and an insufflation manifold for communicating with the gas sealed access port and with a valve sealed access port, wherein the insufflation manifold includes a first outlet line valve for controlling a flow of insufflation gas to the gas sealed access port and a second outlet line valve for controlling a flow of insufflation gas to the valve sealed access port, and wherein at least one of the first and second outlet line valves is a proportional valve configured to dynamically control the flow of insufflation gas. In accordance with a preferred embodiment of the subject invention, the first and the second outlet line valves are both proportional valves.

The subject invention is also directed to a method of surgical gas delivery during a surgical procedure, which includes the steps of: recirculating surgical gas through a gas sealed access port to provide gas sealed access to a body cavity and to maintain a stable cavity pressure during the surgical procedure; and dynamically controlling an outflow of insufflation gas to the body cavity through the gas sealed access port.

These and other features of the gas delivery system of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the gas delivery system and method of the subject invention without undue experimentation, preferred embodiments thereof will be described in detail herein below with reference to the FIGURES wherein:

FIG. 1 is a schematic diagram of the multi-modal gas delivery system of the subject invention, which includes a gaseous sealing manifold for communicating with a gas sealed access port and an insufflation manifold for communicating with the gas sealed access port and with a valve sealed access port, wherein the gas delivery system includes several proportional valves including proportional outlet line valves for dynamically controlling the outflow of insufflation from the insufflation manifold to a patient's body cavity through the gas sealed access port or the valve sealed access port, depending upon a selected operational mode.

DETAILED DESCRIPTION OF THE PREFERRED EMBODIMENTS

Referring now to the drawings wherein like reference numerals identify similar structural elements and features of the subject invention, there is illustrated in FIG. 1 a new and useful multi-modal surgical gas delivery system 10 that is adapted and configured for gas sealed insufflation, recirculation and smoke evacuation during an endoscopic or laparoscopic surgical procedure. The multi-modal surgical gas delivery system 10 of the subject invention includes a gaseous sealing manifold 110 for communicating with a gas sealed access port 20 and an insufflation manifold 210 for communicating with the gas sealed access port 20 and with a valve sealed access port 30.

The gas sealed access port 20 is of the type disclosed in commonly assigned U.S. Pat. No. 8,795,223, which is incorporated herein by reference. The gas sealed access port 20 is adapted and configured to provide gas sealed instrument access to a body cavity, while maintaining a stable pressure within the body cavity (e.g., a stable pneumoperitoneum in the peritoneal or abdominal cavity). In contrast, the valve sealed access port 30 is a conventional or standard trocar, for providing access to a body cavity through a mechanical valve seal, such as, for example, a duckbill seal, septum seal or the like. Depending upon the requirements of a particular surgical procedure, the multi-modal gas delivery system 10 can be utilized with either the gas sealed access port 20, the valve sealed access port 30 or with both access ports 20, 30 at the same time.

The gas delivery system 10 further includes a compressor or positive pressure pump 40 for recirculating surgical gas through the gas sealed access port 20 by way of the gaseous sealing manifold 110. The compressor 40 is preferably driven by a brushless DC (direct-current) motor, which can be advantageously controlled to adjust gas pressure and flow rates within the gas delivery system 10, as disclosed for example in commonly assigned U.S. Pat. No. 10,702,306, which is incorporated herein by reference. Alternatively, the compressor 40 can be driven by an AC motor, but a DC motor will be relatively smaller and lighter, and therefore more advantageous from a manufacturing standpoint.

An intercooler and/or condenser 50 is operatively associated with the compressor 40 for cooling or otherwise conditioning gas recirculating through the gaseous sealing manifold 110. A UVC irradiator 52 is operatively associated with the intercooler or condenser 50 for sterilizing gas recirculating through the internal flow passages 54 formed therein by way of the compressor 40. In addition, the UVC irradiator 52 is intended to sterilize the interior surfaces of the gas conduits or flow passages 54 through which the gas flows within the intercooler/condenser 50.

The UVC irradiator preferably includes at least one LED light source or a florescent light source that is adapted and configured to generate UVC radiation at a wavelength of about between 240-350 nm, and preferably about 265 nm. This ultraviolet light at such a wavelength can sterilize viral, bacterial and microbial bodies within the gas conduits of the system, and can reduce coronavirus including SARS-COV-2.

Preferably, compressor 40, intercooler/condenser 50, gaseous sealing manifold 110 and insufflation manifold 210 are all enclosed within a common housing, which includes a graphical user interface and control electronics, as disclosed for example in commonly assigned U.S. Pat. No. 9,199,047, which is incorporated herein by reference.

The gas delivery system 10 further includes a surgical gas source 60 that communicates with the gaseous sealing manifold 110 and the insufflation manifold 210. The gas source 60 can be a local pressure vessel or a remote supply tank associated with a hospital or healthcare facility. Preferably, gas from the surgical gas source 60 flows through a high pressure regulator 65 and a gas heater 70 before it is delivered to the gaseous sealing manifold 110 and the insufflation manifold 210. Preferably, the high pressure regulator 65 and the gas heater 70 are also enclosed with the compressor 40, intercooler 50, gaseous sealing manifold 110 and insufflation manifold 210 in the common housing.

The gas delivery system 10 further includes a first outlet line valve (OLV1) 212 that is operatively associated with the insufflation manifold 210 for controlling a flow of insufflation gas to the valve sealed access port 30 and a second outlet line valve (OLV2) 214 that is operatively associated with the insufflation manifold 210 for controlling a flow of insufflation gas to the gas sealed access port 20.

In accordance with a preferred embodiment of the subject invention, the first and second outlet line valves 212, 214 of insufflation manifold 210 are proportional valves that are configured to dynamically alter or otherwise control the outflow of insufflation gas to the access ports 20, 30 to match volume fluctuations that may arise in a patient's body cavity as they occur. The first and second proportional outlet line valves 212, 214 provide the gas delivery system 10 with fine control of insufflation gas flow rate to achieve stable flow rates at lower pressure, reduce pressure oscillation and eliminate pneumatic hammer.

Because the first and second proportional outlet line valves 212, 214 are proximal to the patient where flow friction losses are relatively low, the gas delivery system 10 is able to measure peritoneal pressures accurately. Moreover, the use of proportional outlet line valves for this purpose is uniquely possible here, because there is constant gas recirculation throughout the gas delivery system 10, either by way of closed loop smoke evacuation or by way of the gas sealed access port 20.

Proportional valves allow for infinitely variable gas flow adjustment between a minimum flow state and a maximum flow state. Given that some volume changes in a patient's body cavity, such as breathing, are expected and consistent, by employing proportional outlet line valves, the insufflation manifold 210 is able to dynamically alter the gas flow to the body cavity to inverse the expected volume changes, resulting in a neutral effect on the pressure inside the cavity.

An additional benefit of using proportional valves for controlling the outflow of insufflation gas from manifold 210 is a reduction in response time, as compared to that of a solenoid valve. A solenoid valve operates by applying energy to coils, which produces an electromagnetic force that moves a piston. However, the energizing of the coils takes some amount of time, introducing a delay between a commanded action and the physical movement of the piston. In contrast, proportional valves, as employed in the gas delivery system 10 of the subject invention, do not have an energization delay in general, and so they have an improved response time as compared to solenoid valves.

The insufflation manifold 210 further includes a first patient pressure sensor (PWS1) 222 downstream from the first outlet line valve 212 and a second patient pressure sensor (PWS1) 224 downstream from the second outlet line valve 214. These two patient pressure sensors are used to measure abdominal pressure to control outlet line valves 212, 214, respectively. Two other pressure sensors are located upstream from the outlet line valves 212, 214, and are labeled as DPS1 and DPS2. These two pressure sensors are situated within a venturi to measure a pressure differential that is used to infer a total gas flow rate from the insufflation manifold 210 to the patient's body cavity.

A primary proportional valve (PRV) 216 is also operatively associated with insufflation manifold 210 and it is located upstream from the first and second outlet line valves 212, 214 to control the flow of insufflation gas to the first and second outlet line valves 212, 214. Proportional valve 216 functions to maintain an intermediate pressure within the insufflation manifold 210 (as the central node in the LPU) at a constant pressure between 1 and 80 mmHg, dependent on the system operating mode. The opening of PRV 216 can be indirectly initiated by any of the following actions: patient respiration, gas leakage downstream of PRV 216, or the opening of the safety valve LSV 227 or ventilation valve VEV 228, i.e. any event that causes an intermediate pressure to drop. In the system. LSV 227 and VEV 228 are described in more detail below.

The gaseous sealing manifold 110 also includes a high pressure gas fill valve (GFV) 112 that is operatively associated with an outlet side of the compressor 40. GFV 112 is adapted and configured to control gas delivered into the gaseous sealing manifold 110 from the source of surgical gas 60. Preferably, the gas fill valve 112 is a proportional valve that is able to dynamically control surgical gas delivered into the gaseous sealing manifold 110.

The gaseous sealing manifold 110 also includes a smoke evacuation valve (SEV) 114 that is operatively associated with an outlet side of the compressor 40 for dynamically controlling gas flow between the gaseous sealing manifold 110 and the insufflation manifold 210 under certain operating conditions, such as, for example, when the gas delivery device 10 is operating in a smoke evacuation mode. Preferably, the smoke evacuation valve 114 is a proportional valve.

A bypass valve (SPV) 116 is positioned between an outlet side of the compressor 40 and an inlet side of the compressor 40 for controlling gas flow within the gaseous sealing manifold 110 under certain operating conditions. Preferably, the bypass valve 116 is a proportional valve, which is variably opened to establish and control the gaseous seal generated within gas sealed access port 20. Moreover, bypass valve 116 controls gas flow rate to the gaseous seal using feedback from pressure sensors 122, 124, described in further detail below.

The gaseous sealing manifold 110 also includes an air ventilation valve (AVV) 118, which is operatively associated with an inlet side of the compressor 40 for controlling the entrainment of atmospheric air into the system 10 under certain operating conditions. For example, AVV 118 will permit the introduction of atmospheric air into the gaseous sealing circuit to increase the air mass (i.e., the standard volume) within the circuit. The thermodynamics of clinical use conditions can cause a loss of standard volume within the gas circuit. The ventilation valve 118 permits the gas delivery system 10 to make up for this lost volume, in order to ensure that pump pressure and flow rates are sufficient to maintain the gaseous seal within the gas sealed access port 20. The ventilation valve 118 can also be opened to reduce the vacuum side pressure in the gas seal circuit.

An overpressure relief valve (ORV) 120 is operatively associated with an outlet side of the compressor 40 for controlling a release of gas from the system 10 to atmosphere under certain operating conditions. Preferably, the overpressure relief valve 120 is a proportional valve that is opened to reduce the positively pressurized side of the gas seal circuit, especially in the event of an emergency, such as a loss of power to the gas delivery system 10. The normally open configuration of relief valve 120 reduces the risk of over-pressurization of the patient cavity upon loss of power to that valve.

A first pressure sensor (RLS) 122 is operatively associated with an inlet side of the compressor 40 and a second pressure sensor (PLS) 124 is operatively associated with an outlet side of the compressor 40. These pressure sensors 122, 124 are situated to have unobstructed and minimally restricted commutation with the patient's abdominal cavity in order to continuously and accurately measure cavity pressure. The signals from these two pressure sensors 122, 124 are employed by a controller of the gas delivery system 10 to modulate the opening of the two outlet line valves 212 and 214, to control the patient cavity pressure.

In addition, the gaseous sealing manifold 110 includes a gas quality sensor 126 that is operatively associated with an outlet side of the compressor 40. The gas quality sensor monitors the level of oxygen in the recirculation circuit, which corresponds to a concentration of $CO_2$ in the body cavity of a patient, as disclosed in U.S. Pat. No. 9,199,047.

A first blocking valve (BV1) 132 is operatively associated with an outlet flow path of the gaseous sealing manifold 110 and a second blocking valve (BV2) 134 is operatively associated with an inlet flow path to the gaseous sealing manifold 110. The blocking valves 132, 134 are employed during a self-test prior to a surgical procedure, as disclosed in U.S. Pat. No. 9,199,047. It is envisioned that the first and second blocking valves 132, 134 could be are mechanically actuated or pneumatically actuated.

A first filter element 142 is positioned downstream from the first blocking valve 132 for filtering pressurized gas flowing from the compressor 40 to the gas sealed access port 20, and a second filter element 144 is positioned upstream from the second first blocking valve 134 for filtering gas returning to the compressor 40 from the gas sealed access port 20. Preferably, the filter elements 142, 144 are housed within a common filter cartridge, as disclosed for example in U.S. Pat. No. 9,199,047.

The first and second blocking valves 132, 134 communicate with a blocking valve pilot (BVP) 226 that is included within with the insufflation manifold 210. Preferably, the blocking valve pilot 226 is a solenoid valve. It is envisioned that BVP 226 could be fed from the compressor outlet as shown or from a gas source such of surgical gas or air. The insufflation manifold 110 further includes a pressure sensor (PMS) 225 located downstream from the primary proportional valve 216 and upstream from the outlet line valves 212, 214. The two outlet line valves are opened to introduce insufflation gas to the patient's body cavity by way of the access ports 23, 30. This introduction of gas has the effect of increasing pressure within the body cavity. Additionally, the outlet line valves 212, 214 can be opened in conjunction with air ventilation valve 228 to release gas from the body cavity, having the effect of desufflation and reduction of cavity pressure.

The insufflation manifold 210 further includes a low pressure safety valve (LSV) 227 downstream from the primary proportional valve 216 and upstream from the first and second outlet line valves 212, 214 for controlling a release of gas from the system 10 to atmosphere under certain operating conditions. LSV 227 is a purely mechanical valve that functions to limit the maximum intermediate pressure within the manifold 210 or LPU (Low Pressure Unit) in the event of a power interruption, a pressure controller malfunction or if a valve located upstream from the LSV sticks in an open position.

In addition, a ventilation exhaust valve (VEV) 228 is positioned downstream from the primary proportional valve 216 and upstream from the outlet line valves 212, 214 for controlling a release of gas from the system 10 to atmosphere under certain operating conditions. The ventilation exhaust valve 228 is a preferably a proportional valve that is opened to desufflate or otherwise reduce patient cavity pressure. Additionally, VEV 228 can be opened to reduce intermediate pressure within the LPU.

A filter element 242 is positioned downstream from the first outlet line valve 212 for filtering insufflation gas flowing from the insufflation manifold 210 to the valve sealed access port 30. Another filter element 244 is positioned downstream from the second outlet line valve 224 for filtering insulation gas flowing from the insufflation manifold 210 to the gas sealed access port 20. Preferably, filter element 244 is housed with filter elements 142 and 144 in a common filter cartridge, while filter element 242 is separately located.

While the gas delivery system of the subject disclosure has been shown and described with reference to preferred embodiments, those skilled in the art will readily appreciate that changes and/or modifications may be made thereto without departing from the scope of the subject disclosure.

What is claimed is:

1. A surgical gas delivery system for gas sealed insufflation and recirculation comprising:
   a) a gaseous sealing manifold for communicating with a gas sealed access port;
   b) an insufflation manifold for communicating with the gas sealed access port and with a valve sealed access port;
   c) a compressor for recirculating insufflation gas through the gas sealed access port by way of the gaseous sealing manifold;
   d) a first proportional outlet line valve operatively associated with the insufflation manifold for dynamically controlling a flow of the insufflation gas to the gas sealed access port;
   e) a second proportional outlet line valve operatively associated with the insufflation manifold for dynamically controlling a flow of the insufflation gas to the valve sealed access port, wherein the first proportional outlet line valve and the second proportional outlet line valve are configured to dynamically control the flow of the insufflation gas to the gas sealed access port and the flow of the insufflation gas to the valve sealed access port, respectively, to match volume fluctuations in a body cavity of a patient as they occur; and
   f) a primary proportional valve operatively associated with the insufflation manifold, located upstream from the first proportional outlet line valve and the second proportional outlet line valve for controlling the flow of the insufflation gas to the first proportional outlet line valve and the second proportional outlet line valve, and for maintaining an intermediate pressure within the insufflation manifold, wherein the surgical gas delivery system is configured such that when a release valve located downstream from the primary proportional valve and upstream from the first proportional outlet line valve and the second proportional outline valve opens to release the insufflation gas from the surgical gas delivery system to atmosphere, causing an intermediate pressure drop within the insufflation manifold, the primary proportional valve will open to maintain the intermediate pressure within the insufflation manifold.

2. The surgical gas delivery system recited in claim 1, wherein the insufflation manifold includes a first pressure sensor downstream from the first proportional outlet line valve and a second pressure sensor downstream from the second proportional outlet line valve.

3. The surgical gas delivery system recited in claim 2, wherein a pair of pressure sensors are situated upstream from the first proportional outlet line valve and the second proportional outlet line valve to measure a pressure differential that is used to infer a gas flow rate from the insufflation manifold.

4. The surgical gas delivery system recited in claim 1, wherein a source of the insufflation gas communicates with the gaseous sealing manifold and the insufflation manifold.

5. The surgical gas delivery system recited in claim 4, wherein the insufflation gas from the source of the insufflation gas flows through a high pressure regulator and a gas heater before the insufflation gas is delivered to the gaseous sealing manifold and the insufflation manifold.

6. The surgical gas delivery system recited in claim 1, wherein the gaseous sealing manifold includes a gas fill valve operatively associated with an outlet side of the compressor for controlling the insufflation gas delivered into the gaseous sealing manifold from a source of the insufflation gas, and wherein the gas fill valve is a proportional valve.

7. The surgical gas delivery system recited in claim 1, wherein the gaseous sealing manifold includes a smoke evacuation valve operatively associated with an outlet side of the compressor for controlling a gas flow between the gaseous sealing manifold and the insufflation manifold under certain operating conditions, and wherein the smoke evacuation valve is a proportional valve.

8. The surgical gas delivery system recited in claim 1, wherein the gaseous sealing manifold includes a bypass valve between an outlet side of the compressor and an inlet side of the compressor for controlling a gas flow within the gaseous sealing manifold under certain operating conditions, and wherein the bypass valve is a proportional valve.

9. The surgical gas delivery system recited in claim 1, wherein the gaseous sealing manifold includes an air ventilation valve operatively associated with an inlet side of the compressor for controlling entrainment of atmospheric air into the system under certain operating conditions, and wherein the air ventilation valve is a proportional valve.

10. The surgical gas delivery system recited in claim 1, wherein the gaseous sealing manifold includes an overpressure relief valve operatively associated with an outlet side of the compressor for controlling a release of the insufflation gas from the system to atmosphere under certain operating conditions, and wherein the overpressure relief valve is a solenoid valve.

11. The surgical gas delivery system recited in claim 1, wherein the gaseous sealing manifold includes a first pressure sensor operatively associated with an inlet side of the compressor and a second pressure sensor operatively associated with an outlet side of the compressor.

12. The surgical gas delivery system recited in claim 1, wherein the gaseous sealing manifold includes a gas quality sensor operatively associated with an outlet side of the compressor.

13. The surgical gas delivery system recited in claim 1, further comprising a first blocking valve operatively associated with an inlet to the gaseous sealing manifold and a second blocking valve operatively associated with an outlet to the gaseous sealing manifold, and wherein the first blocking valve and the second blocking valve are pneumatically actuated.

14. The surgical gas delivery system recited in claim 13, wherein the first blocking valve and the second blocking valve communicate with a blocking valve pilot included within the insufflation manifold, and wherein the blocking valve pilot is a solenoid valve.

15. The surgical gas delivery system recited in claim 1, wherein the insufflation manifold includes a low pressure safety valve upstream from the first proportional outlet line valve and the second proportional outlet line valve for controlling a release of the insufflation gas from the system to the atmosphere under certain operating conditions.

16. The surgical gas delivery system recited in claim 15, wherein the insufflation manifold includes a ventilation exhaust valve upstream from the first proportional outlet line valve and the second proportional outlet line valve for controlling the release of the insufflation gas from the system to the atmosphere under the certain operating conditions, and the ventilation exhaust valve is a proportional valve.

17. The surgical gas delivery system recited in claim 16, wherein the primary proportional valve is located upstream from the low pressure safety valve and the ventilation exhaust valve.

18. The surgical gas delivery system recited in claim 1, wherein the intermediate pressure is between 1 and 80 mmHg dependent upon a system operating mode.

19. A surgical gas delivery system for gas sealed insufflation and recirculation comprising:
   a) a gaseous sealing manifold for communicating with a gas sealed access port;
   b) a compressor for recirculating insufflation gas through the gas sealed access port by way of the gaseous sealing manifold;
   c) an insufflation manifold for communicating with the gas sealed access port or with a valve sealed access port, wherein the insufflation manifold includes a first outlet line valve for controlling a flow of the insufflation gas to the gas sealed access port and a second outlet line valve for controlling a flow of the insufflation gas to the valve sealed access port, and wherein at least one of the first outlet line valve or the second outlet line valve is a proportional valve configured to dynamically control the flow of the insufflation gas to the gas sealed access port or the flow of the insufflation gas to the valve sealed access port, respectively, so as to match volume fluctuations in a body cavity of a patient as they occur; and
   d) a primary proportional valve included within the insufflation manifold, located upstream from the first outlet line valve and the second outlet line valve for controlling the flow of the insufflation gas to the first outlet line valve and the second outlet line valve and for maintaining an intermediate pressure within the insufflation manifold, wherein the surgical gas delivery system is configured such that when a release valve located downstream from the primary proportional valve and upstream from the first outlet line valve and the second outline valve opens to release the insufflation gas from the surgical gas delivery system to atmosphere, causing an intermediate pressure drop within the insufflation manifold, the primary proportional valve will open to maintain the intermediate pressure within the insufflation manifold.

20. The surgical gas delivery system as recited in claim 19, wherein the first outlet line valve and the second outlet line valve are both proportional valves.

21. The surgical gas delivery system recited in claim 19, wherein the intermediate pressure is between 1 and 80 mmHg dependent upon a system operating mode.

22. A method of surgical gas delivery during a surgical procedure comprising:
   a) recirculating surgical gas through a gas sealed access port to provide gas sealed access to a body cavity and to maintain a stable cavity pressure during the surgical procedure;
   b) dynamically controlling an outflow of insufflation gas to the body cavity through the gas sealed access port by way of a proportional outlet line valve to match volume fluctuations in the body cavity as they occur; and
   c) maintaining a constant pressure upstream from the proportional outlet line valve by way of a primary proportional valve, such that when a release valve located downstream from the primary proportional valve and upstream from the proportional outlet line valve opens to release the insufflation gas to atmosphere, the primary proportional valve will open to maintain the constant pressure.

23. The method recited in claim 22, wherein the constant pressure is between 1 and 80 mmHg.

24. A surgical gas delivery system comprising:
   a manifold including a first outlet line valve for controlling a flow of insufflation gas to a first access port and a second outlet line valve for controlling a flow of the insufflation gas to a second access port, wherein at least one of the first outlet line valve and the second outlet line valve is a proportional valve, and wherein a primary proportional valve is located within the manifold upstream from the first outlet line valve and the second outlet line valve for controlling the flow of the insufflation gas to the first outlet line valve and the second outlet line valve and for maintaining an intermediate pressure within the manifold, whereby opening of the primary proportional valve can be indirectly initiated by an event causing an intermediate pressure drop within the manifold downstream from the primary proportional valve and upstream from the first outlet line valve and the second outlet line valve.

25. The surgical gas delivery system recited in claim 24, wherein the event causing an intermediate pressure drop within the manifold downstream from the primary proportional valve and upstream from the first outlet line valve and the second outlet line valve involves a release valve located downstream from the primary proportional valve and upstream from the first outlet line valve and the second outline valve opening to release the insufflation gas from the surgical gas delivery system to atmosphere.

* * * * *